(12) United States Patent
Franke

(10) Patent No.: US 11,376,436 B2
(45) Date of Patent: Jul. 5, 2022

(54) SYSTEMS AND METHODS FOR PREVENTING NOISE IN AN ELECTRIC WAVEFORM FOR NEURAL STIMULATION, BLOCK, OR SENSING

(71) Applicant: CASE WESTERN RESERVE UNIVERSITY, Cleveland, OH (US)

(72) Inventor: Manfred Franke, Redwood City, CA (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 397 days.

(21) Appl. No.: 16/285,300

(22) Filed: Feb. 26, 2019

(65) Prior Publication Data

US 2019/0184173 A1    Jun. 20, 2019

Related U.S. Application Data

(63) Continuation of application No. 14/707,541, filed on May 8, 2015, now abandoned, which is a
(Continued)

(51) Int. Cl.
*A61N 1/36* (2006.01)
*A61B 5/00* (2006.01)
(Continued)

(52) U.S. Cl.
CPC ............ *A61N 1/36125* (2013.01); *A61B 5/24* (2021.01); *A61B 5/7214* (2013.01);
(Continued)

(58) Field of Classification Search
CPC . A61N 1/36125; A61N 1/36142; H02J 50/12; H02J 50/05; A61B 5/24; A61B 5/7214; A61B 2562/0214
See application file for complete search history.

(56) References Cited

U.S. PATENT DOCUMENTS 3,911,899 A    10/1975 Hattes
4,057,069 A    11/1977 Dorffer et al.
(Continued)

FOREIGN PATENT DOCUMENTS

DE    4324185    1/1995
EP    3606599    2/2020
(Continued)

OTHER PUBLICATIONS

Ackermann, Jr, D. Michael, et al. "Separated interface nerve electrode prevents direct current induced nerve damage." Journal of neuroscience methods 201.1 (2011): 173-176.
(Continued)

*Primary Examiner* — Jared Fureman
*Assistant Examiner* — Michael J Warmflash
(74) *Attorney, Agent, or Firm* — Tarolli, Sundheim, Covell & Tummino LLP

(57) ABSTRACT

One aspect of the present disclosure relates to a system that can prevent unintended signal components (noise) in an electric waveform that can be used for at least one of neural stimulation, block, and/or sensing. The system can include a signal generator to generate a waveform that includes an intended electric waveform and unintended noise. The system can also include a signal transformer device (e.g., a very long wire) comprising a first coil and a second coil. The first coil can be coupled to the signal generator to receive the waveform and remove the unintended noise from the electric waveform. The second coil can pass the electric waveform to an electrode. The second coil can be coupled to a capacitor that can prevent the waveform from developing noise at an electrode/electrolyte interface between an electrode and a nerve.

11 Claims, 12 Drawing Sheets

Related U.S. Application Data continuation-in-part of application No. 14/275,446, filed on May 12, 2014, now Pat. No. 9,205,265.

(60) Provisional application No. 61/821,873, filed on May 10, 2013, provisional application No. 61/824,525, filed on May 17, 2013.

(51) Int. Cl.
*A61B 5/24* (2021.01)
*H02J 50/05* (2016.01)
*H02J 50/12* (2016.01)

(52) U.S. Cl.
CPC .......... *A61N 1/36142* (2013.01); *H02J 50/05* (2016.02); *H02J 50/12* (2016.02); *A61B 2562/0214* (2013.01)

(56) References Cited

U.S. PATENT DOCUMENTS

| | | | |
|---|---|---|---|
| 4,510,936 A * | 4/1985 | Fourcin | A61N 1/36038 607/57 |
| 4,890,618 A * | 1/1990 | Weber | A61F 11/04 607/57 |
| 5,401,970 A | 3/1995 | Kinsey et al. | |
| 5,561,239 A * | 10/1996 | Yasuda | F02P 17/12 73/114.18 |
| 6,293,266 B1 | 9/2001 | Oetting | |
| 6,600,956 B2 * | 7/2003 | Maschino | A61N 1/0556 607/118 |
| 7,620,453 B1 | 11/2009 | Propato et al. | |
| 8,612,002 B2 * | 12/2013 | Faltys | A61N 1/3756 607/116 |
| 9,364,667 B1 * | 6/2016 | Dinsmoor | A61N 1/0524 |
| 9,517,347 B2 * | 12/2016 | Biele | A61N 1/36125 |
| 2002/0120309 A1 | 8/2002 | Richmond et al. | |
| 2007/0043400 A1 | 2/2007 | Donders et al. | |
| 2007/0060815 A1 | 3/2007 | Martin et al. | |
| 2007/0067004 A1 | 3/2007 | Boveja et al. | |
| 2007/0073354 A1 | 3/2007 | Knudson et al. | |
| 2007/0083193 A1 | 4/2007 | Werneth et al. | |
| 2007/0255319 A1 | 11/2007 | Greenberg et al. | |
| 2007/0291522 A1 | 12/2007 | Toba et al. | |
| 2008/0208287 A1 | 8/2008 | Palermo et al. | |
| 2008/0208300 A1 | 8/2008 | Pasch | |
| 2009/0036945 A1 | 2/2009 | Chancellor et al. | |
| 2009/0192567 A1 | 7/2009 | Armstrong et al. | |
| 2009/0254148 A1 | 10/2009 | Borgens et al. | |
| 2011/0021943 A1 | 1/2011 | Lacour et al. | |
| 2011/0071513 A1 | 3/2011 | Shin et al. | |
| 2011/0077660 A1 | 3/2011 | Janik et al. | |
| 2011/0160798 A1 * | 6/2011 | Ackermann, Jr. | A61L 31/048 607/46 |
| 2011/0190849 A1 | 8/2011 | Faltys et al. | |
| 2011/0192720 A1 | 8/2011 | Blauw et al. | |
| 2011/0221438 A1 | 9/2011 | Goodwill et al. | |
| 2012/0016226 A1 | 1/2012 | Gertner | |
| 2012/0053510 A1 | 3/2012 | Peters et al. | |
| 2012/0277829 A1 | 11/2012 | Chow et al. | |
| 2013/0006331 A1 | 1/2013 | Weisgarber et al. | |
| 2013/0035745 A1 | 2/2013 | Ahmed et al. | |
| 2013/0053922 A1 | 2/2013 | Ahmed et al. | |
| 2013/0238048 A1 | 9/2013 | Almendinger et al. | |
| 2013/0274842 A1 | 10/2013 | Gaunt et al. | |
| 2014/0031905 A1 | 1/2014 | Irazoqui et al. | |
| 2014/0119480 A1 | 5/2014 | Keegan | |
| 2014/0324129 A1 | 10/2014 | Franke et al. | |
| 2015/0073406 A1 | 3/2015 | Molsberger | |
| 2015/0165210 A1 | 6/2015 | Kilgore et al. | |
| 2015/0174397 A1 | 6/2015 | Bhadra et al. | |
| 2015/0182742 A1 | 7/2015 | Ackermann et al. | |
| 2015/0238764 A1 * | 8/2015 | Franke | A61N 1/36142 600/377 |
| 2015/0265334 A1 * | 9/2015 | Franke | A61B 18/14 606/34 |
| 2015/0272657 A1 | 10/2015 | Yates et al. | |
| 2016/0101286 A1 | 4/2016 | Bhadra et al. | |
| 2016/0158542 A1 | 6/2016 | Ahmed | |
| 2016/0235969 A1 | 8/2016 | Kilgore et al. | |
| 2016/0235990 A1 | 8/2016 | Mashiach | |
| 2016/0243353 A1 | 8/2016 | Ahmed | |
| 2016/0256689 A1 | 9/2016 | Vallejo et al. | |
| 2016/0263381 A1 | 9/2016 | Ahmed et al. | |
| 2016/0271392 A1 | 9/2016 | Vallejo et al. | |
| 2016/0271413 A1 | 9/2016 | Vallejo et al. | |
| 2016/0331326 A1 | 11/2016 | Xiang et al. | |
| 2016/0346533 A1 | 12/2016 | Bhadra et al. | |
| 2017/0028192 A1 | 2/2017 | Ahmed et al. | |
| 2017/0050024 A1 | 2/2017 | Bhadra et al. | |
| 2017/0080244 A1 | 3/2017 | Chiel et al. | |
| 2017/0100591 A1 | 4/2017 | Nudo et al. | |
| 2017/0136235 A1 | 5/2017 | Molsberger | |
| 2017/0312505 A1 | 11/2017 | Ahmed | |
| 2018/0028824 A1 | 2/2018 | Pivonka et al. | |
| 2018/0256886 A1 | 9/2018 | Bhadra et al. | |
| 2018/0361155 A1 | 12/2018 | Bhadra et al. | |
| 2019/0060640 A1 | 2/2019 | Bhadra et al. | |
| 2019/0167996 A1 | 6/2019 | Bhadra et al. | |
| 2019/0184160 A1 | 6/2019 | Franke et al. | |
| 2019/0184173 A1 | 6/2019 | Franke | |
| 2019/0269921 A1 | 9/2019 | Bhadra et al. | |
| 2019/0314630 A1 | 10/2019 | Ackermann et al. | |
| 2020/0001073 A1 | 1/2020 | Bhadra et al. | |

FOREIGN PATENT DOCUMENTS

| | | |
|---|---|---|
| WO | 2007/082382 | 7/2007 |
| WO | 2008/140376 | 11/2008 |
| WO | 2010/042750 | 4/2010 |
| WO | 2013/188753 | 12/2013 |
| WO | 2015/142838 | 9/2015 |
| WO | 2017/044542 | 3/2017 |
| WO | 2017/062272 | 4/2017 |
| WO | 2017/106519 | 6/2017 |
| WO | 2018/085611 | 5/2018 |
| WO | 2018/187237 | 10/2018 |
| WO | 2019/157285 | 8/2019 |
| WO | 2019/164952 | 8/2019 |
| WO | 2020/010020 | 1/2020 |

OTHER PUBLICATIONS

Bhadra, Niloy, and Kevin L. Kilgore. "Direct current electrical conduction block of peripheral nerve." IEEE Transactions on Neural Systems and Rehabilitation Engineering 12.3 (2004): 313-324.

Borsook, David. "A future without chronic pain: neuroscience and clinical research." Cerebrum: the Dana forum on brain science. vol. 2012. Dana Foundation, 2012.

Brummer, S.B. et al. "Electrical Stimulation of the Nervous System: The Principle of Safe Charge Injection with Noble Metal Electrodes." Bioelectrochemistry and Bioenergetics 2: (1975) 13-25.

Bussel, Catelijne M., Dirk L. Stronks, and Frank JPM Huygen. "Successful treatment of intractable complex regional pain syndrome type I of the knee with dorsal root ganglion stimulation: a case report." Neuromodulation: Technology at the Neural Interface 18.1 (2015): 58-61.

Cogan, S.F., et al. "In Vitro Comparison of the Charge-Injection Limits of Activated Iridium Oxide (AIROF) and Platinum-Iridium Microelectrodes", IEEE Transactions on Biomedical Engineering, 52.9 (2005): 1612-1614.

Cogan, S.F., et al. "Potential-Biased, Asymmetric Waveforms for Charge-Injection With Activated Iridium Oxide (AIROF) Neural Stimulation Electrodes." 2006: 53(2): 327-332.

Donaldson et al. "When are actively balanced biphasic ('Lilly') stimulating pulses necessary in a neurological prosthesis?" Medical & Biological Engineering & Computing Jan. 1986: 24: 41-49.

Elbasiouny, S., et al. Modulation of motoneuronal firing behavior after spinal cord injury using intraspinal microstimulation current pulses: a modeling study. J. Appl. Physiol. 103 (2007) 276-286.

(56) References Cited

OTHER PUBLICATIONS

Fridman, Gene Y., and Charles C. Della Santina. "Safe direct current stimulation to expand capabilities of neural prostheses." IEEE Transactions on Neural Systems and Rehabilitation Engineering 21.2 (2013): 319-328.

Fridman, Gene Y., and Charles C. Della Santina. "Safe direct current stimulator 2: concept and design." In Engineering in Medicine and Biology Society (EMBC), 2013 35th Annual International Conference of the IEEE, pp. 3126-3129. IEEE, 2013.

Gabrielsson, Erik O., et al. "A four diode full wave ionic current rectifier based on bipolar membranes: Overcoming the limit of electrode capacity." Advanced Materials 26.30 (2014): 5143-5147.

Hasegawa, G., et al. "Impact of Electrolyte on Pseudocapacitance and Stability of Porous Titanium Nitride (TIN) Monolithic Electrode", Journal of The Electrochemical Society, 162.1 (2015): A77-A85.

Hollingworth, Milo, et al. "Single Electrode Deep Brain Stimulation with Dual Targeting at Dual Frequency for the Treatment of Chronic Pain: A Case Series and Review of the Literature." Brain sciences 7.1 (2017): 1-11.

Holtzheimer, Paul E., and Helen S. Mayberg. "Deep brain stimulation for psychiatric disorders." Annual review of neuroscience 34 (2011): 289-307.

Huang, C. et al. "Electrical stimulation of the auditory nerve: direct current measurement in vivo." IEEE Transactions on Biomed. Eng. vol. 46 No. Apr. 4, 1999 at 461-470.

Hurlbert, R. John. "Dose-response study of the pathologic effects of chronically applied direct current stimulation on the normal rat spinal cord." J. Neurosurg. 79 (Dec. 1993) 905-916.

Keifer, Orion Paul, Jonathan P. Riley, and Nicholas M. Boulis. "Deep brain stimulation for chronic pain: intracranial targets, clinical outcomes, and trial design considerations." Neurosurgery Clinics 25.4 (2014): 671-692.

Kim et al. "Electrochemical studies on the alternating current corrosion of mild steel under cathodic protection condition in marine environments", Electrochimica Acta 51, 2006, p. 5259-5267.

Krum, Henry, et al. "Catheter-based renal sympathetic denervation for resistant hypertension: a multicentre safety and proof-of-principle cohort study." The Lancet 373.9671 (2009): 1275-1281.

Kumsa, D et al. Electrical neurostimulation with imbalanced waveform mitigates dissolution of platinum Electrodes. J. Neural Eng. 13 (2016): 1-5.

Kumsa, D et al. Electrical neurostimulation with imbalanced waveform mitigates dissolution of platinum electrodes. Neural Eng. (2018) 13(5): 1-8.

Kumsa, D.W., et al. "Electron transfer processes occurring on platinum neural stimulating electrodes: pulsing experiments for cathodic-first, charge-imbalanced, biphasic pulses for 0.566 ? k ? 2.3 in rat subcutaneous tissues", Journal of Neural Engineering, 16 (2019): 1-11.

McHardy, J., et al., "An Approach to Corrosion Control during Electrical Stimulation", Annals of Biomedical Engineering, 5 (1977): 144-149.

Mendell, Lorne M. "Constructing and deconstructing the gate theory of pain." PAIN® 155.2 (2014): 210-216.

Merrill, Daniel R., Marom Blkson, and John GR Jefferys. "Electrical stimulation of excitable tissue: design of efficacious and safe protocols." Journal of neuroscience methods 141.2 (2005): 171-198.

Mortimer, J.T., et al., "Intramuscular Electrical Stimulation: Tissue Damage", Annals of Biomedical Engineering, 8 (1980): 235-244.

Nahin, Richard L. "Estimates of pain prevalence and severity in adults: United States, 2012." The Journal of Pain 16.8 (2015): 769-780.

Nakajima, H., et al. "Cervical angina: a seemingly still neglected symptom of cervical spine disorder?" Spinal cord 44.8 (2006): 509-513.

Neupane, M et al. Study of Anodic Oxide Films of Titanium Fabricated by Voltammetric Technique in Phosphate Buffer Media. Int. J. Electrochem. Sci., 4 (2009) 197-207.

Nielsen et al., "AC-Corrosion and Electrical Equivalent Diagrams", in: Proceedings of 5th International Congress, CeoCo, bruxelles, Belgium, 2000.

Schaldach, M, Fractal Coated Leads: Advanced Surface Technology of Genuiune Sensing and Pacing, Progress in Biomedical Research, (2000): 259-272.

Scheiner, A., et al., "Imbalanced Biphasic Electrical Stimulation: Muscle Tissue Damage", Annals of Biomedical Engineering, 18 (1990): 407-425.

Specht, H. et al., Electrochemical properties and stability of PVD coatings for the application in cardiac and neurological stimulation, (2006).

TjepkemaCloostermans, Marleen C., et al. "Effect of burst stimulation evaluated in patients familiar with spinal cord stimulation." Neuromodulation: Technology at the Neural Interface 19.5 (2016): 492-497.

Yang, Fei, et al. "Differential expression of voltage-gated sodium channels in afferent neurons renders selective neural block by ionic direct current." Science advances 4.4 (2018): eaaq1438 in 10 pages.

\* cited by examiner

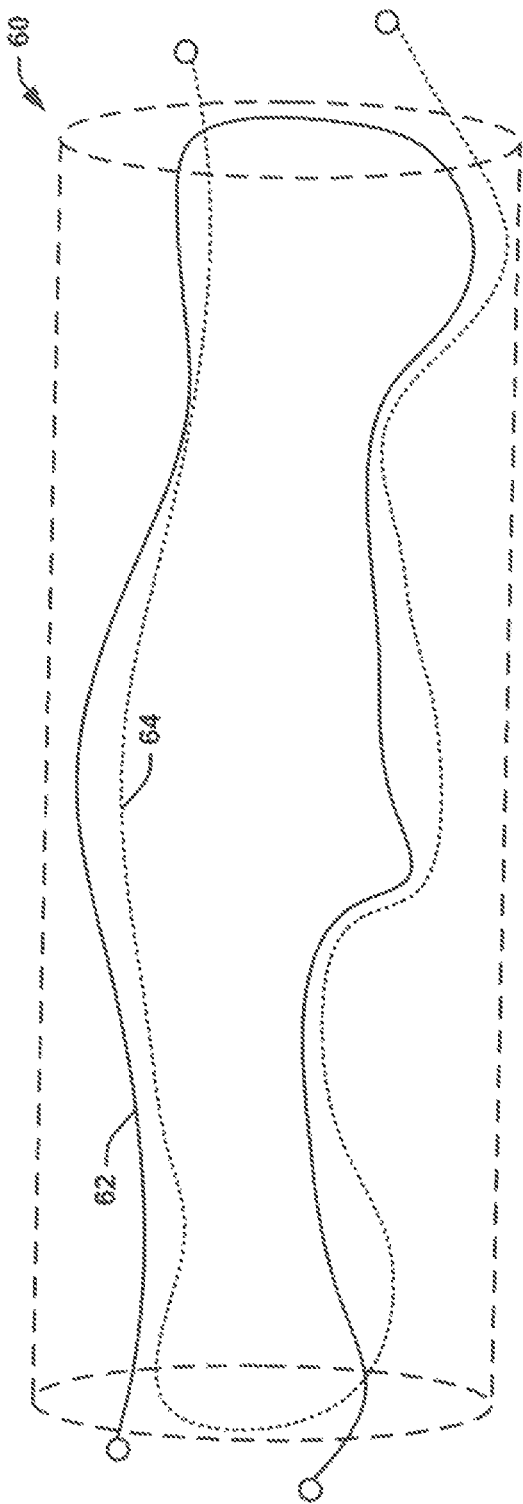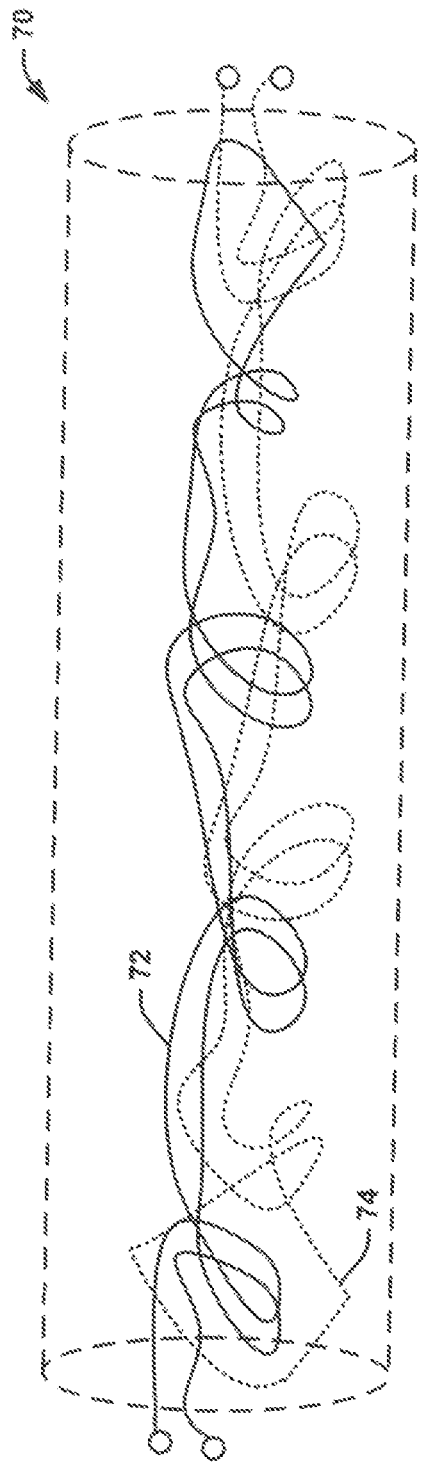

SYSTEMS AND METHODS FOR PREVENTING NOISE IN AN ELECTRIC WAVEFORM FOR NEURAL STIMULATION, BLOCK, OR SENSING

RELATED APPLICATIONS

The present application is a continuation application of U.S. patent application Ser. No. 14/707,541, filed on May 8, 2015, which is a Continuation-in-Part of U.S. patent application Ser. No. 14/275,446 (now U.S. Pat. No. 9,205,265), filed on May 12, 2014 entitled "SYSTEMS AND METHODS FOR REMOVING CONTAMINATING NOISE FROM AN ELECTRIC WAVEFORM FOR NEURAL STIMULATION AND NERVE BLOCK", which claims the benefit of U.S. Provisional Application No. 61/821,873, filed May 10, 2013, entitled "LC-BLOCKING-AND-DC-BALANCING CIRCUIT." This application also claims the benefit of U.S. Provisional Application No. 61/824,525, filed May 17, 2013, entitled "BALANCED ELECTRODE SYSTEM." The entirety of these applications is hereby incorporated by reference by all purposes.

This application is also related to U.S. Provisional Application No. 61/933,433, filed Jan. 30, 2013, entitled "METHODS AND DEVICE FOR MITIGATING OR PREVENTING DC CURRENTS IN NEURAL STIMULATION," hereinafter "the '433 provisional." The entirety of this application is hereby incorporated by reference for all purposes.

TECHNICAL FIELD

The present disclosure relates generally to neural stimulation, block, and/or sensing, and, more specifically, to systems and methods that can prevent noise in an electric waveform that can be used for neural stimulation, block, and/or sensing.

BACKGROUND

High-frequency alternating current waveforms in the kilohertz range (KHFAC) can provide temporary nerve conduction block that does not provide lasting effect on conduction. Unintentional DC signals can contaminate KHFAC waveforms, leading to unexpected nerve block and/or damage. Like KHFAC waveforms, direct current (DC) signals also can block conduction in the nerve. However, even at small amplitudes (e.g., in a low micro Ampere ($\mu$A) range), after prolonged or repeated application, such DC signals can damage the nerve tissue. For example, the DC signals can cause a lasting effect nerve on conduction, which can be noticeable as a persistent reduction in nerve conductivity, even after the application of any kind of electric waveform has ended. This persistent reduction in nerve conductivity can be related to changes in pH levels at and/or within the nerve in close proximity to the electrode (e.g., near the electrode/electrolyte interface), and can coincide with the damage of neural tissue.

To substantially mitigate unintentional signal components from the electric waveform, techniques like additional capacitance and/or shunting resistance can be applied between the signal generator and the electrode. However, these approaches are not feasible and/or not practical for use with higher frequency waveforms like KHFAC waveforms, especially current-controlled KHFAC waveforms. For example, the higher frequency waveforms do not allow the capacitors sufficient time to discharge the DC imbalance between stimulation pluses, so the unintentional DC signals that contaminate the KHFAC waveforms cannot be substantially eliminated.

SUMMARY

The present disclosure relates generally to neural stimulation, block, and/or sensing, and, more specifically, to systems and methods that can prevent noise in an electric waveform that can be used for neural stimulation, block, and/or sensing. For example, stimulation generators can generate electric waveforms that can be contaminated with unintentional signal components (e.g., direct current ("DC") signals) that can damage the nerve. In another example, unintentional signal components (e.g., DC voltage potentials) can develop between two electrode contacts with different material characteristics (e.g., size, shape, surface area, roughness, material, etc.), which can reduce the signal to noise ratio (SNR). The systems and methods of the present disclosure can mitigate the effects of these DC signals by ensuring that the electric waveform that reaches the nerve is not contaminated with the DC signals.

In one aspect, the present disclosure can include a system to prevent noise in an electric waveform that can be used for at least one of neural stimulation, block, and sensing. The system can include a signal generator to generate a waveform that includes an intended electric waveform and unintended noise. The system can also include a signal transformer device comprising a first coil and a second coil. The first coil can be coupled to the signal generator to receive the waveform and remove the unintended noise from the electric waveform. The second coil can pass the electric waveform to an electrode. The second coil can be coupled to a capacitor that can prevent the waveform from developing noise at an electrode/electrolyte interface between an electrode and a nerve.

In another aspect, the present disclosure can include a system for neural stimulation, block, and sensing. The system can include a signal generator that generates a waveform. The waveform can include a plurality of frequency components. The signal generator can send the waveform through the primary unit (e.g., a coil or winding of wires), which can pass the waveform to a plurality of secondary units, each coupled to an electrode. Each of the secondary units can be tuned to a different resonance frequency to be operated based on a unique frequency component of the waveform, while allowing for maximum transfer of energy from the primary unit to a chosen secondary unit. In other words, several signals can be transmitted from the signal generator to individual electrodes in parallel at different frequency bands.

In a further aspect, the present disclosure can include a method for avoiding saturation during neural stimulation or block. The method can include receiving, into a first coil of a signal transformer device, an electrical waveform from a signal generator device. The first coil of the signal transformer device can prevent saturation of an output stage of the signal generator device. The method can also include passing, into a second coil of the signal transformer device, the electrical waveform to at least one of a plurality of electrodes. The second coil can be coupled to a capacitor that can prevent saturation of an amplification component or can prevent the distortion of the waveform as a result of a saturation of the amplification component.

In yet another aspect, the present disclosure can include a method for avoiding distortion of a neural signal acquired by one of a plurality of electrodes. During signal acquisition, the neural signal can become distorted if a potential difference exists between at least two of the plurality of electrodes. For example, the potential difference can exist because the two electrodes can each form an electrode/electrolyte half cell connected through an amplification circuit to form a full cell (or battery-like structure). A primary coil, with or without additional circuit components (e.g., resistor, inductor, or capacitor) can allow further tuning of the resonance frequency of the primary sensory circuit, ensuring the capture of true neural signals by ensuring the absence of DC voltage potential differences between the plurality of electrodes. In a further implementation, tuning the primary coil with additional capacitive, resistive and/or inductive components can allow for the increased specificity for neural signals in a certain frequency band. Such a passive filter can filter neural signals during the process of signal acquisition without the need or with significantly reduced need for additional power to accomplish a first step of filtering of signals acquired by one of the plurality of the electrodes.

In yet another instance, the present disclosure can include a system to selectively filter and/or selectively pass signal components of a waveform generated by a signal generator to one or a plurality of electrodes for neural stimulation or block. Such a system can allow a physician to adapt the amount of electric signal energy long after implantation to selectively interface with neural tissue simply by modifying the one signal's frequency and/or amplitude. Choosing one, a set of or all electrodes implanted into a patient to receive specific components of an electric waveform can be achieved by modifying the one signal's frequency components to match the tuning frequency of secondary coils (with additional components) attached to electrodes intended for neural stimulation and/or block.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIGS. 9-10 are schematic diagrams showing example electrode leads that can be used in the systems shown in FIGS. 1-3;

DETAILED DESCRIPTION

I. Definitions

Figure 1:
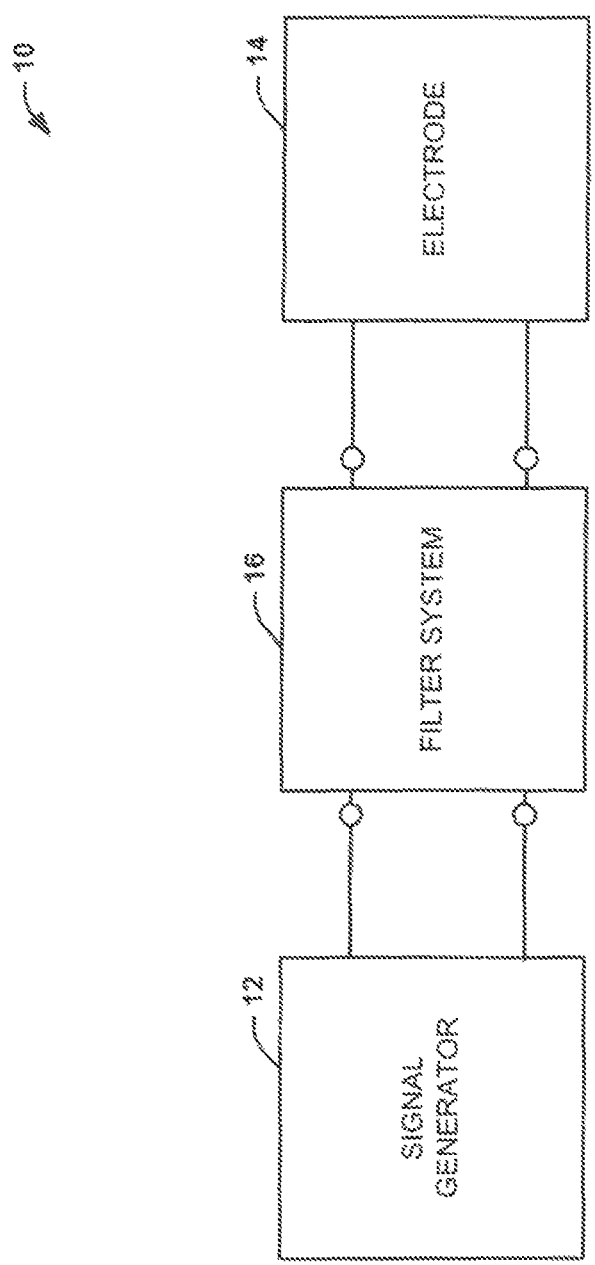
FIGS. 1-3 are schematic block diagrams showing systems that can prevent noise in an electric waveform that can be used for neural stimulation, block, and/or sensing, in accordance with an aspect of the present disclosure.

In the context of the present disclosure, singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items. Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "signal transformer" can refer to a device (e.g., transformer or other device including multiple coupled coils) that can provide a frequency-dependent electric impedance for filters in neural stimulation and nerve block applications, as well as for filtering noise in applications in sensing neural or muscular signals (e.g., electroneurogram (ENG), electromyogram (EMG), electrooculogram (EOG), etc.). In some instances, the signal transformer can include at least two electro-magnetically coupled coils (e.g., a primary coil and a secondary coil), each with two connectors. The two connectors of the primary coil can represent the input connection of the signal transformer and the two connectors of the secondary coil (or any additional coils on the non-primary side) can represent the output connection of the signal transformer. The primary coil and/or the secondary coil can be coupled to one or more additional circuit components. In some instances, a primary coil can be in the form of a continuous cable with windings. For example, the primary coil can have certain locations/areas with significantly more windings per lead unit length than at other locations/areas.

As used herein, the term "neural prosthesis" or "neural prosthetic" can refer to one or more devices that can substitute for a neurological function (e.g., motor function, sensory function, cognitive function, etc.) that has been damaged (e.g., as a result of a neurological disorder). For example, a neural prosthesis can include a stimulation device that restores neurological function ("neural stimulation") and/or a blocking device that blocks nerve conduction ("nerve block"). The term "stimulation waveform," as used herein, can encompass an electrical waveform used for neural stimulation and an electrical waveform used for nerve block.

As used herein, the term "nerve" can refer to a "peripheral nerve." Generally, a peripheral nerve can refer to a nerve in a patient's body other than brain and spinal cord. A peripheral nerve can include a bundle of fibers (including motor and sensory fibers) that can connect the brain and spinal cord to the rest of the patient's body. For example, a peripheral nerve can control the functions of sensation, movement, and motor coordination. In some instances, the peripheral nerve can conduct information bi-directionally (e.g., providing both motor control and sensory feedback).

As used herein, the terms electric waveform "stimulation waveform", and "electrical waveform" can refer to an electrical signal that can be generated by a waveform generator and applied to the nerve with an electrode to achieve neural stimulation or nerve block. In some instances, the electrical waveform can be a mathematical description of a change in voltage over time (or "voltage controlled") or a change in current over time (or "current controlled"). In some instances, the electric waveform can be a biphasic waveform. In other instances, the electric waveform can be a monophasic waveform.

As used herein, the term "biphasic waveform" can refer to an electric waveform that includes both an anodic phase of the waveform and a cathodic phase. The anodic phase and the cathodic phase can be applied in either order. Examples of biphasic waveforms can include a pulsed waveform, a high frequency electric alternating current (KHFAC) waveform (e.g., in the kilohertz frequency range), a charge-balanced direct current (CBDC) waveform, or a multi-phased direct current (MPDC) waveform.

As used herein, the term "monophasic waveform" can refer to an electric waveform that includes a single phase of the waveform. The monophasic waveform can include a single anodic phase or cathodic phase. In some instances, a monophasic waveform can include a signal waveform shape that modulates a carrier waveform of significantly higher frequency.

As used herein, the terms "signal generator," "waveform generator," and "stimulator" can refer to a device that can generate the electric waveform that can be provided to an electrode. In some instances, the signal generator can include contaminating noise with the electric waveform. The signal generator can be, for example, implanted within a patient's body or external to the patient's body.

As used herein, the term "electrode" can refer to a device that provides an attachment for one or more contacts. The one or more contacts can be made of an interface material providing the conversion of current flow via electrons in a metal (wire/lead) to ionic means (in an electrolyte, such as interstitial fluid). In some instances, the electrode can aid in shaping the electric field generated by the contacts.

The signal generator can be connected to the electrode via one or more leads. As used herein, the term "lead" can refer to an electrical connection between an electrode and the signal generator and/or a filter.

As used herein, the term "noise" can refer to any unintended component of a signal that is not the intended signal (e.g., the electrical waveform). In some instances, noise can be a component of the signal that contaminates or obscures the intended signal (e.g., generated by the signal generator and/or established at the electrode/electrolyte interface). Although noise can be irregular, it tends to have an average frequency. The average frequency can be a low frequency and/or high frequency. For example, low frequency noise can have a lower frequency than an electrical waveform used for neural stimulation, block and/or sensing (e.g., DC contamination, zero Hertz noise). In another example, high frequency noise can have a higher frequency than the electrical waveform used for neural stimulation, and/or nerve block. The term "unintentional signal components" can be used herein interchangeably with "noise".

As used herein, the term "electrode/electrolyte interface" can refer to a double layer interface where a potential difference is established between the electrode and the electrolyte (e.g., due to charge transfer). When the electrode is placed in contact with the nerve, the electrolyte can be the area of the patient's body surrounding the nerve.

As used herein, the term "tuning" can refer to adjusting or adapting an electrode to receive a portion of a signal having a certain resonance frequency.

As used herein, the term "resonance frequency" can refer to a frequency capable of exciting a resonance maximum of a given electrode. In some instances, the electric waveform can have a plurality of resonance frequencies. In some instances, the terms "resonance frequency" and "tuning frequency" can be, used interchangeably.

As used herein, the term "saturation" can refer to a voltage drift from the zero line toward one of the voltage rails of an amplification circuit. In some instances, the saturation can pertain to an amplification circuit processing neural input sensed from the biological organism. In other instances, the saturation can pertain to an amplification circuit of an output unit.

As used herein, the term "substantially eliminate" can refer to a complete (e.g., 100%) or partial (e.g., less than 100%, such as about 90%, about 80%, about 70%, about 60%, or less than about 50%) elimination of unintended noise from an intended electric waveform. The terms "substantially eliminate" and "eliminate" can be used interchangeably herein.

As used herein, when energy is transferred between two electrodes "preferentially," the term "preferentially" can refer to 55%, 60%, 65%, 70%, 75%, 80%, 85%, 90%, 95% or up to 99.999% of the energy being transferred to one electrode, while the other electrode only receives 45%, 40%, 36%, 30%, 25%, 20%, 15%, 10%, 5% or less than 0.1% of the energy. It will be understood that the preferential transfer of energy can happen between any number of electrodes, and the preferential electrode can receive greater than or equal to 55% of the energy being transferred.

As used herein, the terms "patient" and "subject" can refer to any warm-blooded organism in need of neural stimulation, block, and/or sensing. Example warm-blooded organisms can include, but are not limited to, a human being, a pig, a rat, a mouse, a dog, a cat, a goat, a sheep, a horse, a monkey, an ape, a rabbit, a cow, etc.

II. Overview

The present disclosure relates generally to neural stimulation, block, and/or sensing, and, more specifically, to systems and methods that can prevent noise in an electric waveform that can be used for neural stimulation, block, and/or sensing. In some instances, commercially available and/or real-world signal generators can produce noise (e.g., small unintended DC components) that is added to intended electric waveforms due to an imperfect balancing at an output stage of the signal generator. When used over a prolonged time period, noise can damage the signal generator, the electrode, and/or the nerve. Noise can also result when different signals are generated simultaneously to operate different electrodes. Transmitting a frequency-selective alternating current signal can prevent the development of these DC components.

Typically, in-line capacitors and/or shunting resistors can be used to filter such unintended noise from the intended electric waveform. However, this approach is not feasible for continuously ongoing stimulation (e.g., high frequency alternating current stimulation with kilohertz frequency (KHFAC) waveforms), since there is no inter-stimulation-interval that allows for shorting the accumulated charge within the in-line capacitors. However, a transformer, including at least two inductive coils that are electromagnetically coupled, was placed in parallel with the stimulator and the electrode with a capacitor coupled to one of the coils, the noise can be compensated for automatically, thereby protecting the signal generator, the electrode, and the nerve tissue.

III. Systems

One aspect of the present disclosure, as shown in FIG. 1, can include a system 10 that can prevent noise in an electric waveform that can be used for neural stimulation, block, and/or sensing. When used herein, the term "prevent" can refer to preventing, removing, reducing, and/or minimizing noise. The electric waveform can be used in applications, such as neural stimulation, block, and/or sensing. For example, the system 10 can be embodied within a neural prosthesis device to provide the neural stimulation, block, and/or sensing. Although neural stimulation, block, and sensing are described herein, it will be understood that noise can be prevented in electric waveforms used for other applications.

The system 10 can include at least a signal generator 12 and an electrode 14 in parallel with a filter system 16. The signal generator 12 can generate a signal that includes an electric waveform (intended) contaminated with noise (unintended). In some instances, the signal generator 12 can be a machine that generates an electric waveform for neural stimulation or block. In other instances, the signal generator 12 can be a portion of a patient's body that generates a signal for a sensing application. The electric waveform generated by the signal generator 12 can be a voltage controlled waveform or a current controlled waveform. The electric waveform can be contaminated with noise from the signal generator 12. In some instances, the electric waveform can be a biphasic waveform. Although most biphasic waveforms are intended to be charge-balanced, in some instances, the electric waveform generated by the signal generator 12, especially when the electric waveform is over a high frequency, can be contaminated with a small DC component that eventually causes the stimulator to "run the signal into the rails". In other instances, the biphasic waveform can be intended to be an unbalanced charge biphasic waveform. In other instances, the electric waveform can be a monophasic waveform.

The electrode 14 can apply the electric waveform to the nerve. The noise from the signal generator should be eliminated before it reaches the electrode 14. Additionally, the electrode 14 can establish an electrode/electrolyte interface with a portion of a patient's body surrounding the nerve. Noise can be created at the electrode-electrolyte interface. This noise can damage the nerve through changes in pH and resulting electrochemical reactions.

The electrode 14 can include one or more contacts that, in some instances, can be made of the same or different materials. For example, the contacts can be tuned to different resonance frequencies to apply different components of the electric signal to the nerve. In some instances, the electrode 14 can apply the electric waveform to the nerve for neural stimulation and or nerve block. In other instances, the electrode can receive a sensed signal from the nerve and send an electric signal to a device for further processing of the signal. For example, the electrode 14 can be a nerve shaping electrode, an electrode array, a spiral electrode, a cuff electrode, a Huntington style electrode, a co-linear placed spinal cord stimulation (SCS) or deep brain stimulation (DBS) electrode, a disk electrode, an intra-muscular electrode, or an intra-fascicular electrode.

To remove the noise from the signal generator 12 and to ensure that noise is not developed at the contacts of the electrode 14, a filter system 16 can be placed between the signal generator and the electrode. In some instances, the filter system 16 can include passive circuit components (e.g., fixed or variable capacitors, resistors, and/or inductors). The filter system 16 made entirely of passive components can be of a small size to save size and weight.

Figure 2:
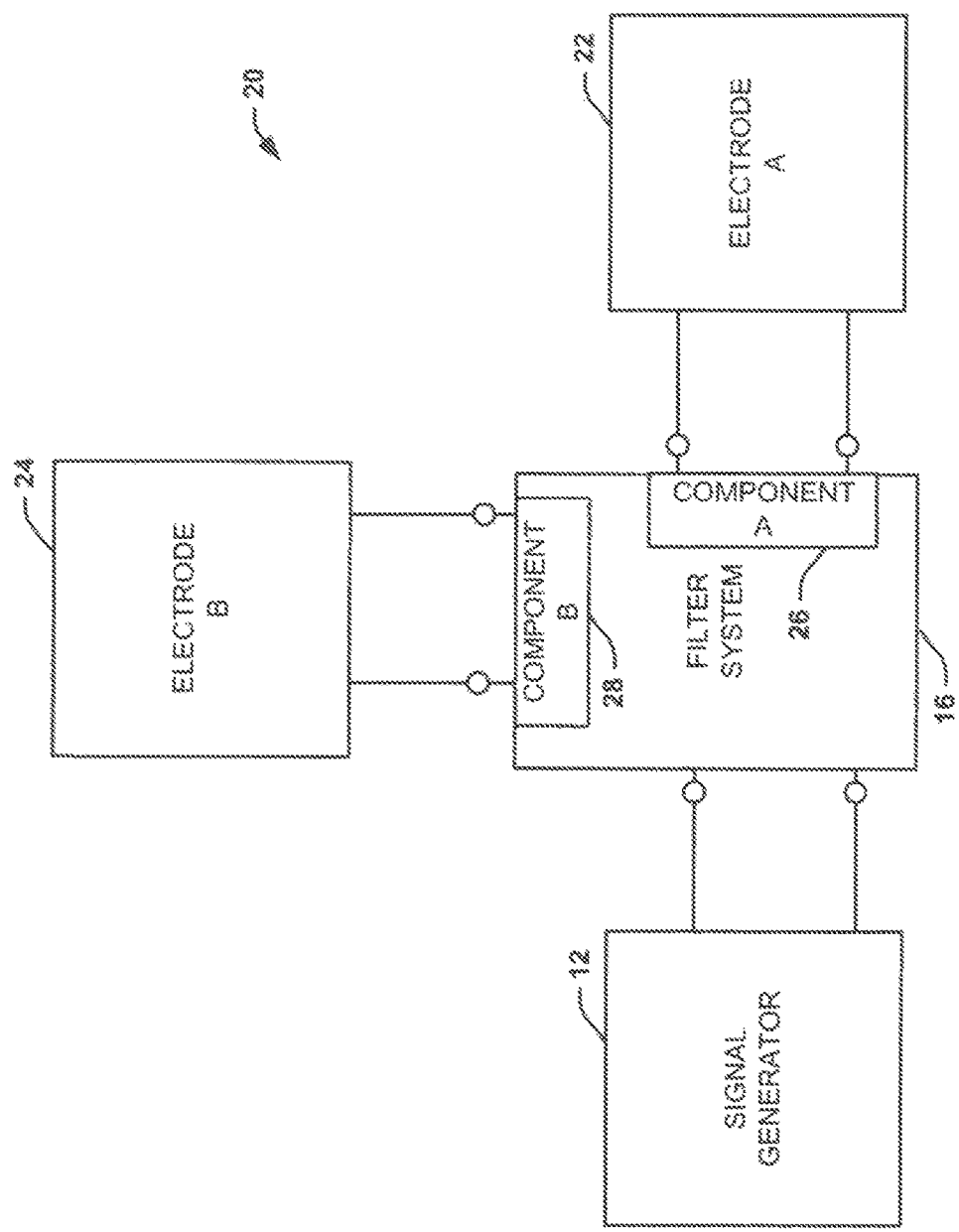

FIG. 2 shows another system 20 that can prevent noise in an electric waveform. System 20 can include a signal generator 12 and more than one electrode (e.g., electrode A 22 and electrode B 24 in this example) that are each connected to a filter system 16. The signal generator 12 can generate a signal that can include a combination of signal 1 at frequency 1 and signal 2 at frequency 2. The waveform energy can be coupled preferentially to one of the electrodes 22, 24. For example, frequency 1 of signal 1 can match a resonance frequency of one of the filter's secondary set of components (e.g., component A 26, which is coupled to electrode A 22), but does not match the resonance frequency of the other one of the filter's secondary components (e.g., component B 28, which is coupled to electrode B 24). In this example, the energy from the waveform, being preferentially sent to component A 26, can be preferentially provided to electrode A 22, but not to electrode B 24.

Figure 3:
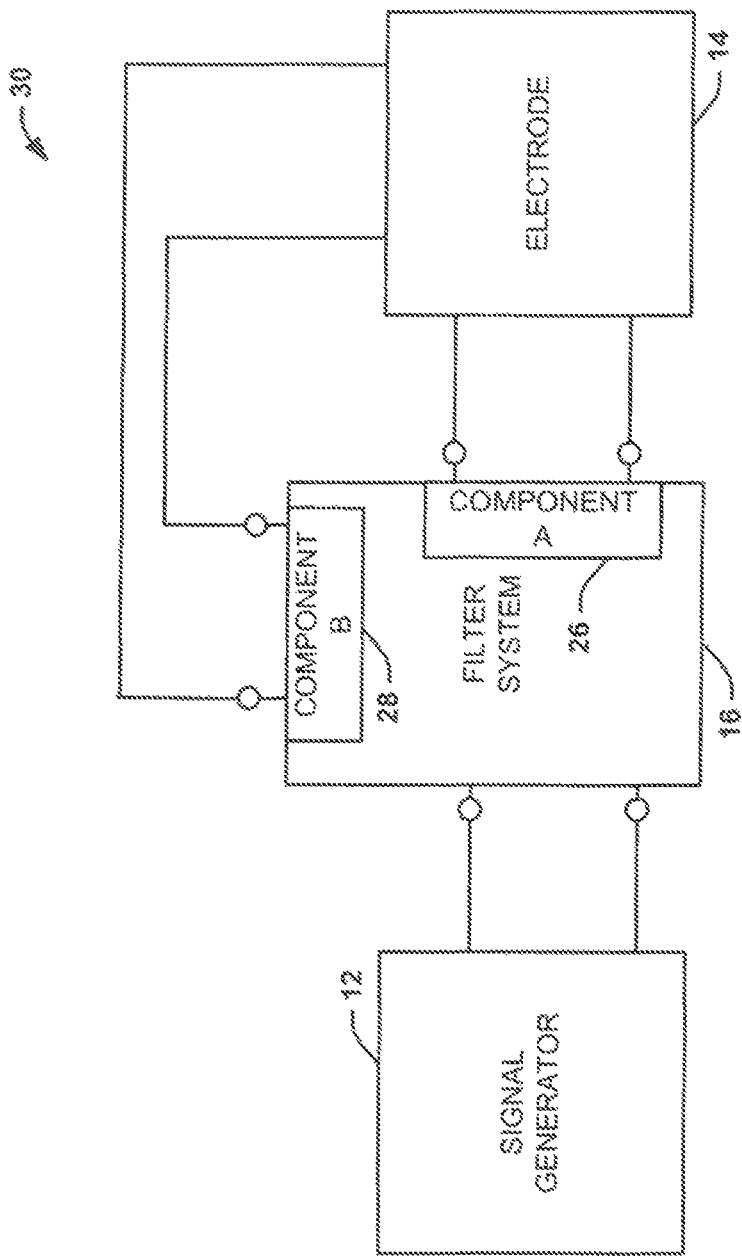

In the system 20 of FIG. 2, the outputs of the filter system 16 are connected to different electrodes (electrode A 22 and electrode B 24). In this case, the electrodes 22, 24 can be operated at different voltage or current levels based on the selection of the output frequency of the signal generator 12. However, as shown in FIG. 3, the outputs of the filter system 16 are connected to the same electrode 14 (or electrodes). By connecting the filter system 16 to the same electrode, a doubling in stimulation voltage can be achieved at the electrode simply by changing the output frequency of the signal generator 12.

Examples of the filter system 16 are shown in FIGS. 4-8. Although each figure is drawn with a core separating inductors. In some instances, the core separating the inductors can be light-weight (e.g., composed of air, a rare earth element, or the like). In fact, due to the light-weight core, the packing volume and weight of the filter system 16 can be significantly reduced compared to other filters, such as the secondary-side-open-transformer-inductors (SOTI).

Figure 4:
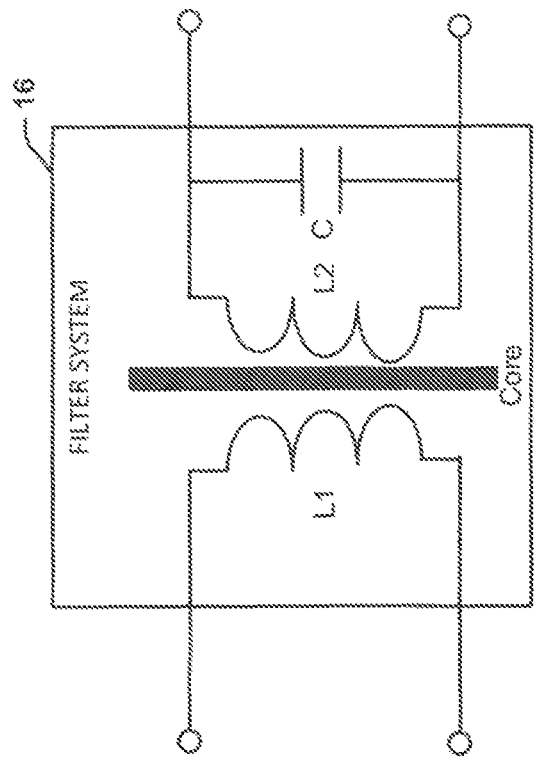
FIGS. 4-8 are schematic diagrams showing example circuit configurations of the filter system shown in FIGS. 1-3.

The filter system 16, as shown in FIG. 4, can include a signal transformer that includes at feast two inductors (L1, L2) separated by a core and a capacitor coupled to the second of the at least two inductors (L2). The first inductor or primary-side inductor (L2), located on the signal generator 12 side of the core, can filter the nose from the signal generator 12. The capacitor coupled to the second or secondary side inductor (L2), located on the electrode 14 side of the core, can prevent noise from being established at the electrode/electrolyte interface and/or between the contacts of the electrode 14.

The at least two inductors (L1, L2) can be inductive coils that are electromagnetically coupled together. In some instances, the capacitor can have a capacitance that is much smaller than the capacitance of the electrode/electrolyte interface that is established near the neural tissue. For example, the capacitor can have a capacitance that is no more than $1/5$ of the capacitance of the electrode/electrolyte interface (e.g., no larger than 0.1 µF.) Even in cases where the electrode 14 includes contacts of different materials, establishing two different half-cells, the capacitor (C) can prevent noise (e.g., a continuous DC flow) at the electrode-electrolyte interface, preventing the electrode from running into Fermi potentials that cause dissolution of the electrode contact and or a change in the electrolyte pH, which can cause damage to the nerve.

In instances where the electric waveform is a monophasic waveform, the filter system 16 can output a charge balanced biphasic waveform with the noise minimized. Accordingly, the signal generator 12 need only generate the monophasic waveform and the filter system 16 can generate a charge balanced biphasic waveform to deliver to the electrode 14. This can reduce the power consumption associated with the generation of the waveform. In cases where the electric waveform is already biphasic, the filter system 16 can balance the charge between the phases of the biphasic waveform to output a balanced charge biphasic waveform with the noise minimized to the electrode 14. For instance, the filter system 16 can provide offset charge compensation to ensure that the biphasic waveform is charge balanced before delivery to the electrode 14.

Figure 5:
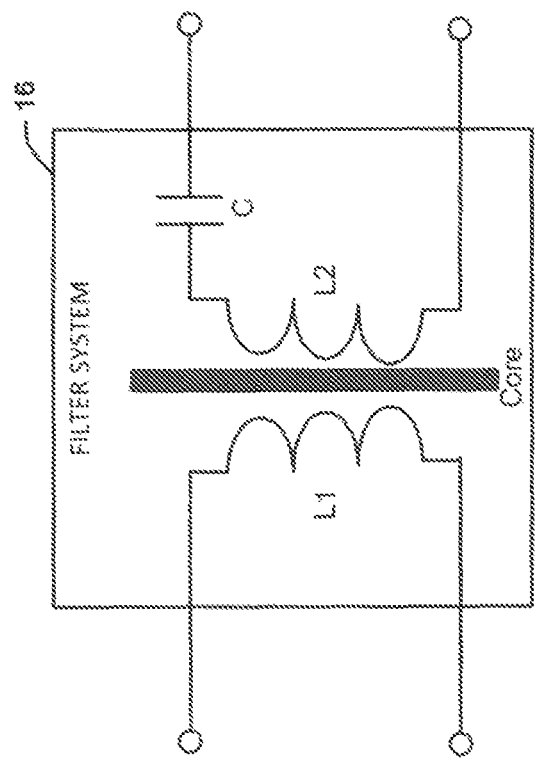

In FIG. 4, the capacitor (C) is coupled to the second inductor (L2) in series. However, in other instances, as shown in FIG. 5, the capacitor (C) can be coupled to the second inductor (L2) in parallel. When the capacitor is coupled in parallel to the second inductor, the filter system 16 can provide tuning to one or more specific frequencies, so that certain frequencies get passed to the electrode 14 or filtered preferentially. Additionally, when the capacitor is coupled in parallel, the noise can be actively monitored and removed by a feedback circuit (e.g., an OpAmp feedback circuit).

Figure 6:
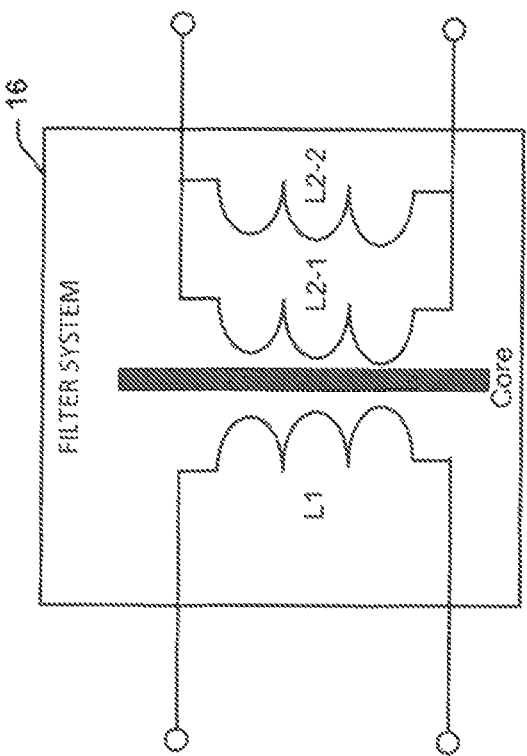

In some instances, as shown in FIG. 6, the second inductor (L2) can include two or more inductive coils (L2-1, L2-2) in parallel. Although not illustrated, the inductive coils can be coupled to the capacitor (C) in series (FIG. 2) and/or in parallel (FIG. 3). In some instances, the filter system 16 with the two or more inductive coils (L2-1, L2-2) on the second side can act as a voltage doubler. The two or more inductive coils (L2-1, L2-2) can be coupled to the same electrode 14, but have different tuning frequencies. One coil can act as a voltage doubler for the other coil, so that if the frequency is changed to the second coil's tuning frequency, the stimulation is possible with twice the voltage. Accordingly, by changing the stimulation frequency, the electrode 14 can be stimulated with two different voltage requirements, while still using the same hardware and same low voltage rail on the signal generator 12 side.

Figure 7:
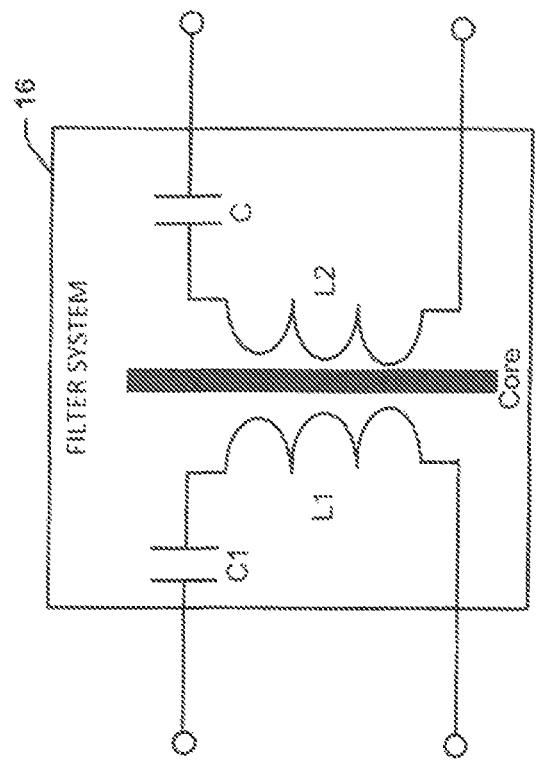

In other instances, as shown in FIG. 7, the first inductor (L1) can be coupled to capacitor (C1). Although a capacitor (C1) is illustrated, the first inductor (L1) can, additionally or alternatively, be coupled to a resistor or an inductor. The capacitor, resistor, or inductor can have a fixed value or a variable value. The circuit component coupled to the first inductor (L1) can be used to adjust a tuning frequency for electromagnetic coupling from the first coil (L1) to the secondary coil (L2) (or coils (L2-1. L2-2)). Additionally, in some instances, the noise that can be stored on the capacitor on the first side can be measured and corrected using a feedback loop (e.g., an OpAmp feedback loop). Additionally, although not shown, the second inductor (L2) can be coupled to additional fixed or variable circuit components (e.g., capacitor, resistor, inductor) to adjust a tuning frequency for the electromagnetic coupling to the first coils.

Figure 8:
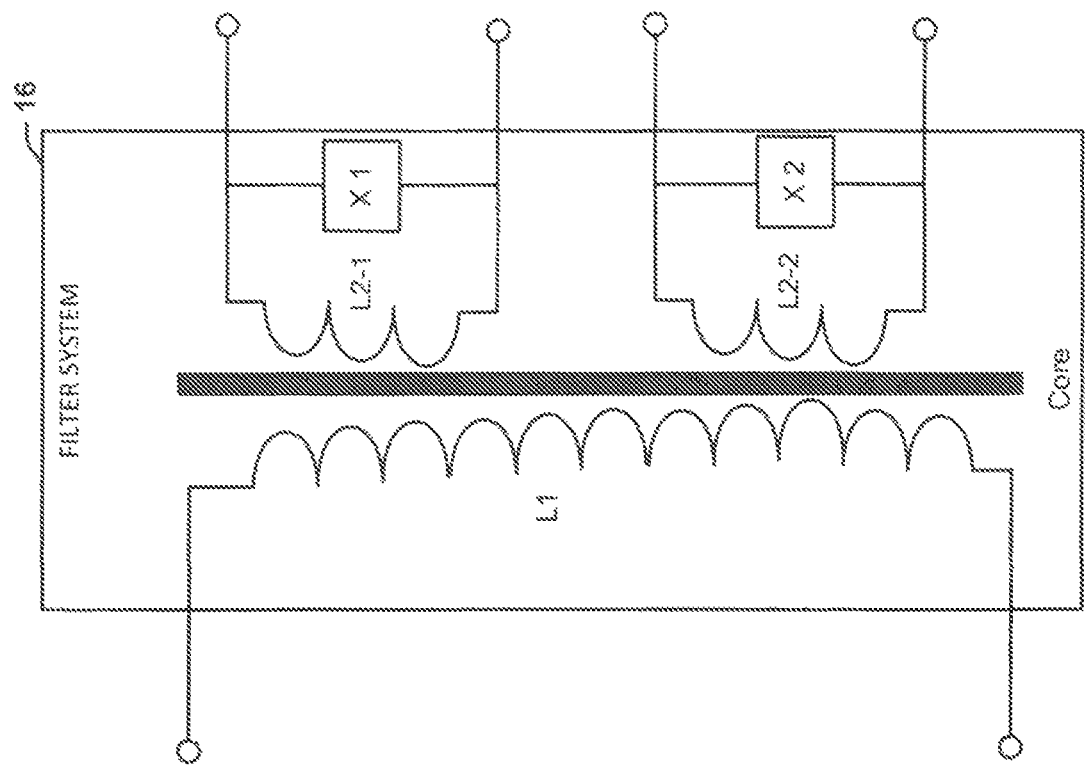

In still other instances, as shown in FIG. 8, the secondary side of the core can include two or more inductors (L2-1, L2-2). Each of the inductors can be coupled to one or more additional circuit components (X1, X2) tuned to different resonance frequencies. For example, the additional circuit components (X1, X2) can include a combination in series or parallel of one or more resistors, one or more capacitors, and/or one or more inductors.

In some instances, it electrodes can be coupled to the outputs of X1 and X2. In this case, the electrodes can be operated at different voltage or current levels. If the coupling ratio of the windings of L1 to L2-1 is about 1, but the coupling ratio of the in of L1 to L2-2 is about 0.5, then an input voltage of Y volts on the electrode coupled to L2-1 would result in the same output voltage of Y volts on L2-1 and 0.5 Y volts on L2-2 (at 100% coupling by 100% matching of the signal generator output frequency to the L2-1 and L2-2 tuning frequency). In other instances, both outputs of X1 and X2 can be coupled to the same electrode, which (under the same conditions) can result in a doubling in stimulation voltage simply by changing the generator output frequency. Indeed, an input waveform with multiple voltages can switch the output range of a given generator circuit by simply changing the frequency.

FIGS. 9 and 10 illustrate different leads that can be used to connect to the signal generator 12 to the electrode 14 or electrodes 22, 24. In some instances, the leads can represent the filter system 16 to eliminate noise from the electrical signal. The leads can include an insulating cable housing coupled metallic conductors 62, 64 and 72, 74. The metallic conductors 62, 64 and 72, 74 can be electro-magnetically, inductively, and/or capacitively coupled. A core to enhance coupling can be present, absent, or present only at specific locations.

The metallic conductors 62, 64 and 72, 74 can transmit and de-couple electric waveform to from the signal generator 12 to the electrode 14. In some instances, metallic cables 62, 64 and 72, 74 can reside inside of an insulating cable without touching each other. The metallic cables can be separated by a certain distance (e.g., 1 mm). In some instances (e.g., when high voltages like 100 V are required), the individual leads can have an additional insulator (e.g., a 5 μm poly-imide coating on at least a portion of the metallic conductors) beyond the insulating cable itself near the respective leads so that the leads are not short circuited. There is no faradic connection through the at least because the metallic conductor entering the cable on one side 62, 72 (also referred to as the primary side, primary cable, or the like) and 64, 74 (also referred to as the secondary side, secondary cable, or the like) does not exit the other end of the cable. Instead, the metallic cables 62 and 64 and 72 and 74 are coupled together (e.g., electro-magnetic, inductive, ands/or capacitive) happens only inside the cable. In some instances, the plurality of leads can include one primary coil and a plurality of secondary cables inductively coupled to the primary coil, which is shared by all of the plurality of secondary coils. In other instances, the primary coil can include two of the cables in the lead and the secondary cable is made up of the other two cables in the lead, so that the lead itself has four thin wires that are inductively coupled.

In some instances, the coupling can be mostly inductive. The conductors can be wound around each other (e.g., FIG. 10) and/or lay very close to each other as a loop (e.g., FIG. 9) or a single wire (e.g., with a return path through the casing of an implantable signal generator) so that the lead is essentially a transformer. The core of the conductor can be fortified with ferrite or any other ferro-magnetic substance to increase the electromagnetic coupling between the primary side 62, 72 and the secondary side 64, 74. The stimulation current through the electrode can be transmitted inductively from the signal generator 12 through the lead's primary line (e.g., 62, 72) and transmitted to the electrode by the lead's secondary line (e.g., 64, 74).

In other instances, the coupling can be mostly capacitive. The conductors inside the cable can be close to each other, but not necessarily wound around each other. To achieve the transmission of the signal mostly through capacitive effects, the conductors can be manufactured as thin metallic sheets that are passivized and then molded together without a faradic connection. In some instances, the metallic sheets can be separated by a dielectric substance (e.g., a substance with a high dielectric constant). The surface area of the conductors can be further increased in some instances by an electro-chemical process, such as Pt black on Pt wires, so that the conductors can have an increased capacity.

Figure 11:
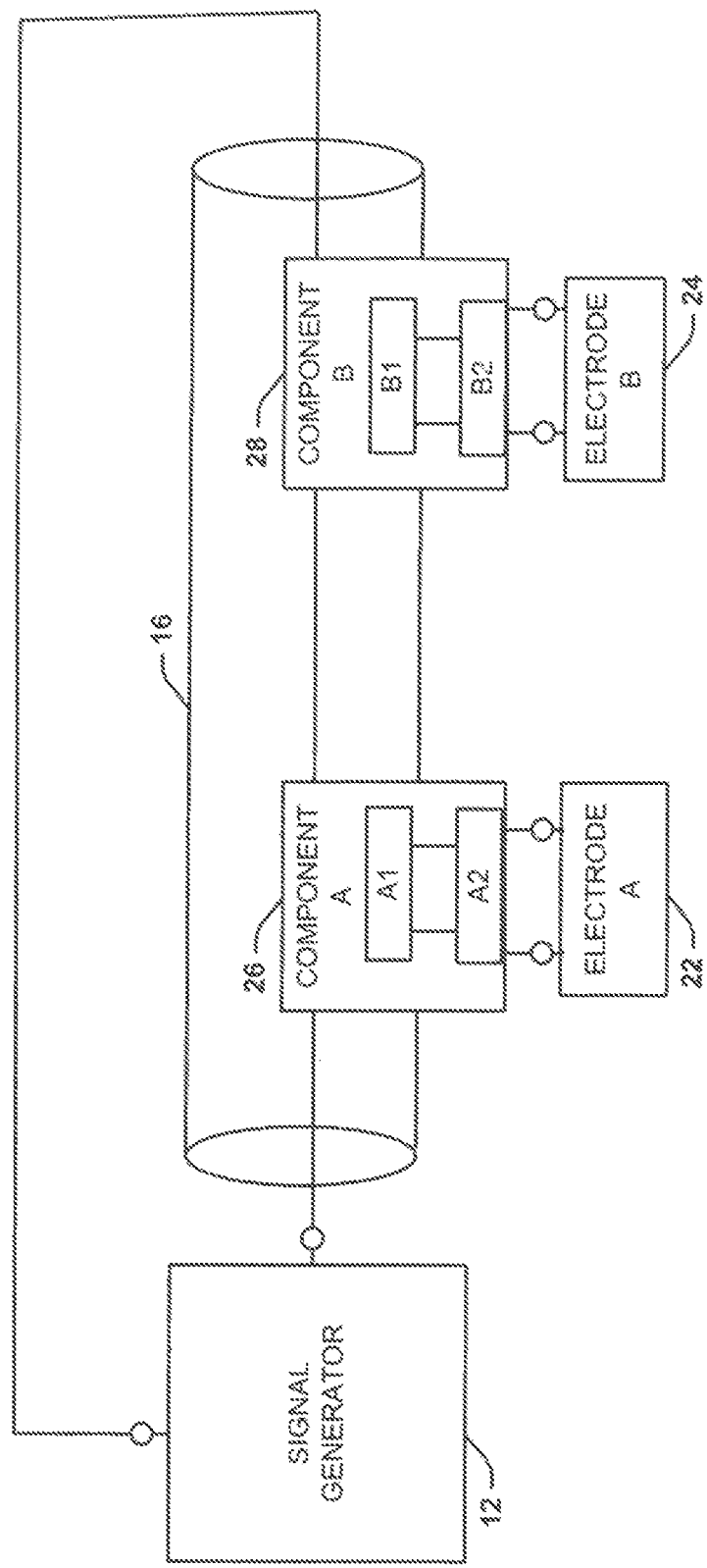
FIGS. 11 and 12 are schematic diagrams showing a modular implementation of the system in FIGS. 1-3.
Figure 12:
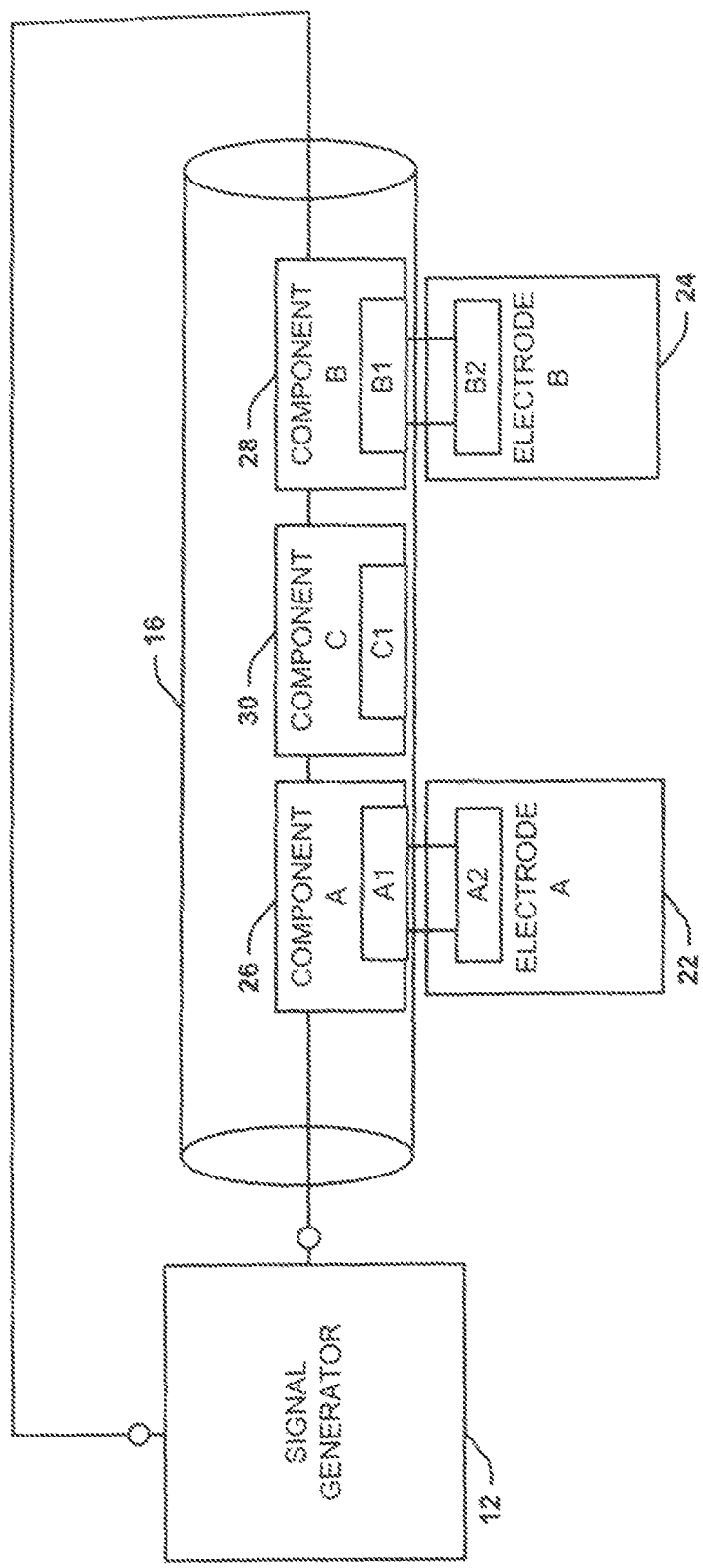

In some instances, as described, for example, in the '433 provisional, the inductive or capacitive coupling can be limited to specific locations that represent only a small portion of the entire length of the cable, as shown, for example, in FIGS. 11 and 12. The cable can be a normal wire for some distance and an inductance for specific locations representing the primary coil of the coupling. The secondary coil can be immovably attached to the housing of the primary coil, as shown in FIG. 11, and/or could be modular, which can allow a physician to make the decision of which tuning system is selected for the secondary set of components, as shown in FIG. 12.

Signals intended for neural stimulation or block may have varying signal components that allow for the selective passage of some but not all signal components from the signal generator to one or a plurality of electrodes. Selective activation of electrodes based on changing the signal composition may provide a physician with the ability to adapt the electric energy provided to select electrodes and modify the ratio of energy transfer to one or more electrodes by changing the signal or signal's carrier frequency. For example, the physician can selectively transfer electric energy to one or more electrodes by varying the output signal frequency or frequency components of the signal generator 12. The specific tuning frequency of each secondary coil can provide for a selecting filtering of some and selective passing of other frequency components from the signal generator to select electrodes.

IV. Methods

Figure 13:
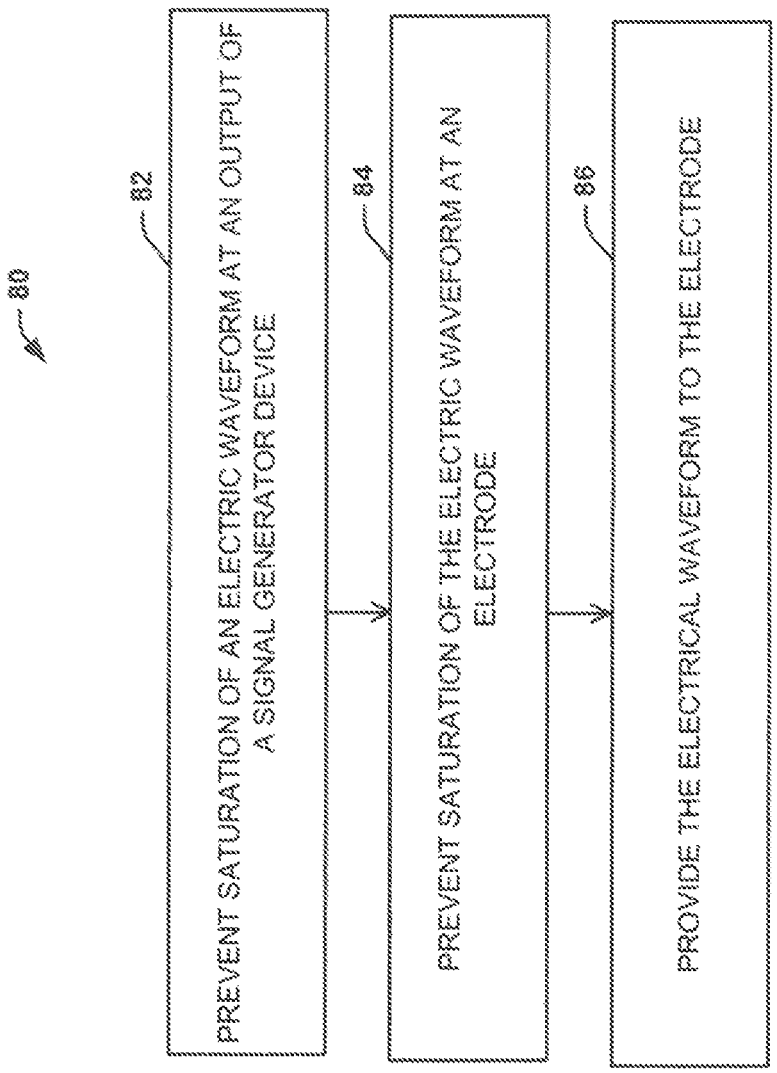
FIG. 13 is a process flow diagram showing a method for preventing saturation of an electric waveform, in accordance with another aspect of the present disclosure.

Another aspect of the present disclosure can include methods that can that can prevent noise in an electric waveform that can be used for neural stimulation, block, and/or sensing, according to an aspect of the present disclosure. An example of a method 80 that can prevent saturation of the electric waveform is shown in FIG. 13. Another example of a method 90 that can prevent a DC-offset from developing in the electric waveform in shown in FIG. 14. Yet another example of a method 100 that can filter different resonance frequencies of the electric waveform to different electrodes is shown in FIG. 15. The methods 80-100 can each be implemented by systems 10-30 as shown in FIGS. 1-3.

Figure 14:
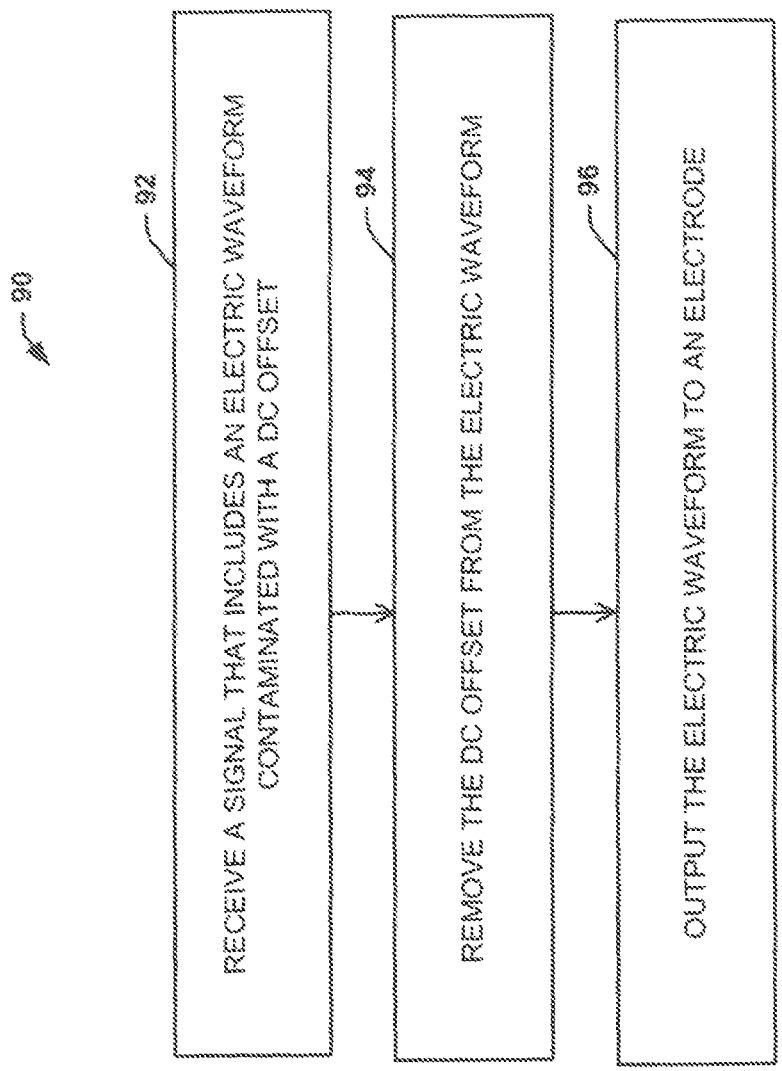
FIG. 14 is a process flow diagram showing a method for preventing noise in an electric waveform that can be used for neural stimulation, block and/or sensing, in accordance with yet another aspect of the present disclosure.
Figure 15:
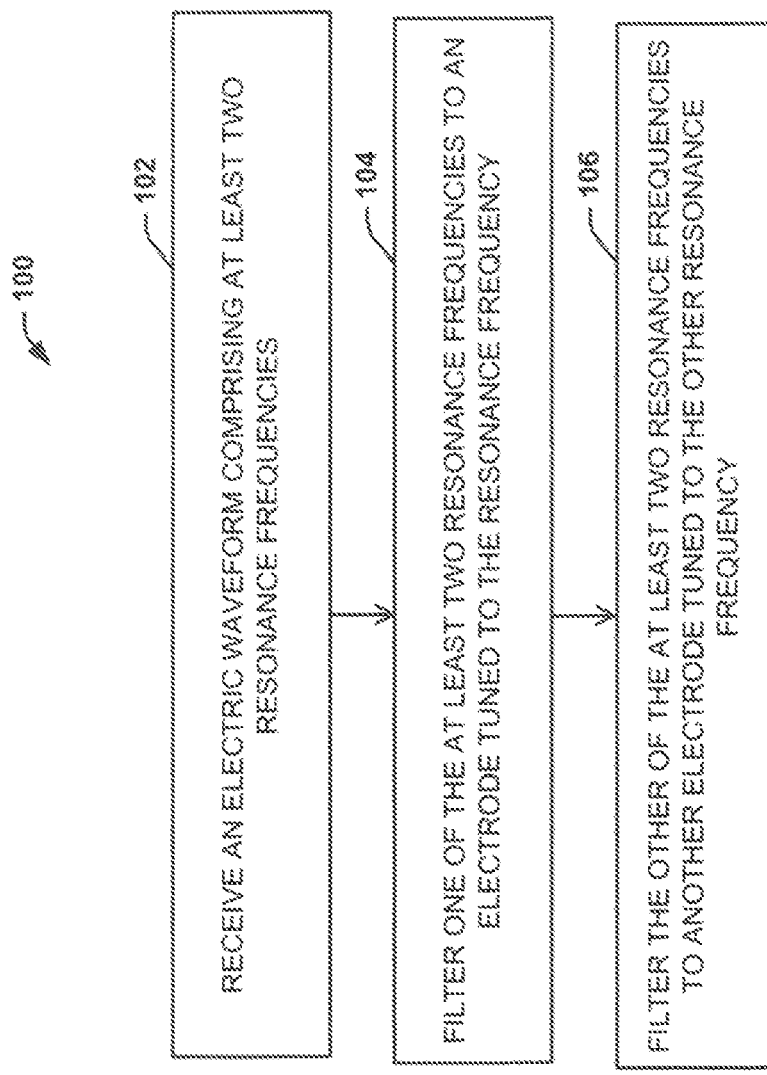
FIG. 15 is a process flow diagram showing a method for filtering different resonance frequencies of an electric waveform to different electrodes, in accordance with still another aspect of the present disclosure.

The methods 80-100 as shown in FIGS. 13-15 are illustrated as process flow diagrams with flowchart illustrations. For purposes of simplicity, the methods 80-100 are shown and described as being executed serially; however, it is to be understood and appreciated that the present disclosure is not limited by the illustrated order as some steps could occur in different orders and/or concurrently with other steps shown and described herein. For example, one or more of the steps of the method can be executed in parallel, although they are shown in the drawings as executing serially. Moreover, not all illustrated aspects may be required to implement the methods 80-100.

Referring to FIG. 13, an aspect of the present disclosure can include a method 80 for preventing saturation of an electric waveform. For example, method 80 can be used during neural stimulation, block, and/or sensing. As noted, the method 80 can be implemented by the system 10 as shown in FIG. 1, in which a filter system 16 can be placed between a signal generator 12 and an electrode 14. The electrode 14 can include a plurality of electrodes and/or electrode contacts.

The method 80 can include receiving (e.g., by a first coil (L1) of the filter system 16) an electrical waveform from the signal generator. At 82, saturation of the electric waveform can be prevented at an output of a signal generator device (e.g., by the first coil (L1)). For example, the first coil can prevent the signal generator from entering an amplification stage, which can lead to saturation of the signal generator's output stage.

The electric waveform can be inductively transmitted between coils of the filter device. At 84, saturation of the electric waveform can be prevented at the electrode (e.g., by the capacitor (C) coupled to the second coil (L2)). The saturation can be prevented at the capacitive part of the electrode/electrolyte interface and could distort the electric waveform if noise (e.g., DC contamination) accumulates between contact materials of different materials or different configurations. At 86, the electrical waveform can be provided to the electrode. Accordingly, the electric waveform can be passed (e.g., by a second coil (L2) of the filter system 16) to the electrode, while preventing saturation at the electrode.

Referring to FIG. 14, another aspect of the present disclosure can include a method 90 for preventing a DC-offset (an example of, a type of noise) from developing in an electric waveform. For example, method 90 can be used during neural stimulation, bock, and/or sensing. As noted, the method 90 can be implemented by the system 10 as shown in FIG. 1 in which filter system 16 can be placed between a signal generator 12 and an electrode 14 to prevent the DC-offset from developing in the waveform.

At 92, a signal (e.g., from signal generator 12) can be received (e.g., by filter system 16) that includes an electric waveform that can be contaminated with a DC offset. The electric waveform can be a voltage controlled waveform or a current controlled waveform. In some instances, the electric waveform can be a charge-balanced biphasic waveform or a charge-unbalanced biphasic waveform. In other instances, the electric waveform can be a monophasic waveform. Although the monophasic waveform or the charge-balanced biphasic waveform can be damaging when applied to a nerve, the monophasic waveform or the charge-unbalanced waveform provides the advantages of lower power consumption by the signal generator. The filter system can be configured to ensure that the electrical waveform that reaches the electrode is a change-balanced biphasic waveform. The filter system can include a primary coil and a secondary coil that can be coupled to a capacitor. In some instances, the second coil can be coupled to the capacitor in series. In other instances, the second coil can be coupled to the capacitor in parallel. The capacitor coupled to the second coil in parallel can provide tuning to certain frequencies, such that certain frequencies get passed or filtered preferentially. Additionally, the first coil and/or the second coil can be coupled to additional fixed or adjustable circuit components (e.g., resistors, capacitors, and/or inductors) to adjust the tuning frequency of the electromagnetic coupling between the first coil and the second coil in the filter system.

At 94, the DC offset can be removed (e.g., by a second coil (L2) coupled to a capacitor (C) in filter system 16) from the electric waveform. In instances where the electric waveform is a monophasic waveform, the filter system can create a charge-balanced biphasic waveform from the monophasic waveform. In instances where the electric waveform is a biphasic waveform, the filter system can involve ensuring that the biphasic waveform is a charge-balanced biphasic waveform. For example filtering the biphasic waveform can compensate for an offset charge compensation t provide the charge-balanced biphasic waveform.

In some instances, when the capacitor coupled to the second coil in parallel, the DC offset can be measured actively across the capacitor and a feedback circuit (e.g., an OpAmp feedback circuit) can be used to compensate for the DC offset before the waveform is of to an electrode. To minimize the DC offset, the capacitor can be much smaller than the capacitance of the electrode/electrolyte interface that is established near the neural tissue. For example, the capacitor can have a capacitance that is no more than ⅕ of the capacitance of the electrode/electrolyte interface. For example, the capacitance can be no larger than 0.1 µF.

At 96, the electric waveform can be output to the electrode (e.g., electrode 14). Removing the DC offset from the electric waveform can protect the signal generator, the electrode, and/or the surrounding nerve tissue from damage inherent to the contamination by the DC offset. For example, since the electric waveform that reaches the electrode is no longer contaminated by DC components, the health of the neural tissue can be preserved because a change in pH in proximity to the electrode is prevented. Changing the pH can cause electrochemical damage to the nerve tissue and/or the electrode. As another example, the DC offset can send the signal generator into an amplification stage, which can cause the signal generator to run into the rails or saturate, causing the signal generator to not work correctly.

Referring now to FIG. 15, Illustrated is a method 100 for filtering different resonance frequencies of an electric waveform to different electrodes. For example, method 100 can be used during neural stimulation, block, and/or sensing. As noted, the method 100 can be implemented by the system 10 as shown in FIG. 1, in which a filter system 16 can be placed between a signal generator 12 and an electrode 14 (which can include a plurality of contacts). The electrode can be connected to the filter system by a plurality of leads. The filter system and/or the leads can filter the different resonance frequencies to different electrodes.

At 102, an electric waveform can be received (e.g., from the signal generator). The electric waveform can include signals with two resonance frequencies. In fact, the electric waveform can have a multitude of resonance frequencies (e.g., any number greater than or equal to two). At 104, one of the resonance frequencies can be filtered (e.g., by filter system 16) to an electrode contact (e.g., of electrode 14) tuned to the resonance frequency. At 106, the other of the resonance frequencies can be filtered to another electrode tuned to the other resonance frequency. In some instances, a physician can be given the choice of implantable coupling ratio between the signal generator and the coupled electrode systems to increase versatility with the same signal generator.

In other instances a physician can choose to attach two secondary coils of varying winding ratios to primary coils of the lead and electrically couple the secondary coils in parallel before attaching them to an electrode. Such a system would allow the frequency selective stimulation of the same electrode with different voltages. If the signal frequency aligns to the tuning frequency of the first of the two secondary coils, then a voltage level A is fed to the electrode. If the signal frequency aligns to the tuning frequency of the second of the two secondary coils, then a voltage level B is fed to the electrode. This method of selecting stimulation voltages based on signal frequency may increase the versatility of an implanted system to react to changes in electrode impedances to the neural tissue due to encapsulation or mechanical movement.

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

What is claimed is:

1. A system for neural stimulation, block, or sensing, the system comprising:
a lead configured to couple a plurality of electrodes to a signal generator, the lead comprising a primary unit comprising a winding of a plurality of wires and a secondary unit comprising another set of a plurality of wires, each tuned to a different resonance frequency band;
wherein the signal generator is configured to generate a waveform having a plurality of frequency bands, and provide the waveform to the primary unit;
wherein each electrode of the plurality of electrodes connected to a respective one of the plurality of wires, each electrode configured to be operated at a respective different resonance frequency band;
wherein each of the plurality of electrodes is configured to be selectively activated to transfer electric energy based on the respective different resonance frequency band;
wherein a mechanical attachment between the primary unit and the secondary unit facilitates a stable inductive coupling of electric energy from the signal generator to the plurality of electrodes without a direct faradaic connection between the signal generator and the plurality of electrodes; and
wherein the lead provides the mechanical coupling by an insulator that allows permanent or temporary attachment, loosening, and reattachment of the secondary unit to various locations on the primary unit.

2. The system of claim 1, wherein an inductive coupling between the primary unit and the secondary unit facilitates a voltage multiplication to the at least one of the plurality of electrodes by frequency-selective activation.

3. The system of claim 1, wherein the lead further comprises an insulating cable housing surrounding a plurality of coupled metallic conductors.

4. The system of claim 3, wherein the plurality of coupled metallic conductors are coupled together by at least one of an electro-magnetic coupling, an inductive coupling, or a capacitive coupling.

5. The system of claim 4, wherein the coupling is mostly a capacitive coupling and the coupled metallic conductors further comprise a plurality of passivized metallic sheets separated by at least one dielectric substance.

6. The system of claim 4, wherein the coupling is mostly an inductive coupling and the coupled metallic conductors are at least one of wound around each other or positioned close to each other as a loop to form a transformer.

7. The system of claim 1, wherein the system is configured to at least one of prevent, remove, reduce, or minimize noise in the waveform.

8. The system of claim 1, wherein the waveform is at least one of a voltage controlled waveform, a current controlled waveform, a biphasic waveform, or a monophasic waveform.

9. The system of claim 1, wherein the plurality of electrodes are configured to establish an electrode/electrolyte interface with a portion of a patient's body surrounding a nerve.

10. The system of claim 9, wherein the first unit and the second unit are configured to remove noise at the electrode/electrolyte interface and/or between contacts of the plurality of electrodes.

11. The system of claim 1, wherein the plurality of electrodes comprises at least a nerve shaping electrode, an electrode array, a spiral electrode, a cuff electrode, a Huntington style electrode, a co-linear placed spinal cord stimulation electrode, a deep brain stimulation electrode, a disk electrode, an intra-muscular electrode, or an intra-fascicular electrode.

\* \* \* \* \*